United States Patent
Sakai et al.

(10) Patent No.: US 7,332,522 B2
(45) Date of Patent: Feb. 19, 2008

(54) LIVER FUNCTION PROTECTING OR AMELIORATING AGENT

(75) Inventors: Yasushi Sakai, Tsukuba (JP); Shun Kayahashi, Tsukuba (JP); Erika Hashizume, Tsukuba (JP); Ryusuke Nakagiri, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 233 days.

(21) Appl. No.: 10/473,867

(22) PCT Filed: Mar. 28, 2002

(86) PCT No.: PCT/JP02/03098

§ 371 (c)(1),
(2), (4) Date: Oct. 3, 2003

(87) PCT Pub. No.: WO02/080904

PCT Pub. Date: Oct. 17, 2002

(65) Prior Publication Data

US 2004/0122085 A1    Jun. 24, 2004

(30) Foreign Application Priority Data

Apr. 5, 2001    (JP) ............ 2001-106600

(51) Int. Cl.
*A61K 31/34* (2006.01)
*A61K 31/343* (2006.01)

(52) U.S. Cl. .......... 514/457; 514/470; 549/283

(58) Field of Classification Search ........ 549/283, 549/290, 307, 289; 514/457, 470
See application file for complete search history.

(56) References Cited

U.S. PATENT DOCUMENTS 5,281,721 A * 1/1994 Powers et al. ............ 549/23

OTHER PUBLICATIONS

Sotoyama, Shouhin to Kagaku (1979), 21(3), Jul. 1996 (Chem. Abstract).*
Tome, Aliment Pharmacol Ther. vol. 19 pp. 707-714 (2004).*
Madhotra, Q.J.Med. vol. 96 pp. 391-400 (2003).*
Arteel, PubMed abstract Gastroenterology 124(3): 778-90 2003.*

* cited by examiner

Primary Examiner—Janet L. Andres
Assistant Examiner—Raymond Covington
(74) Attorney, Agent, or Firm—Antonelli, Terry, Stout & Kraus, LLP.

(57) ABSTRACT

A liver function protecting or improving agent which comprises a compound represented by the formula (I)

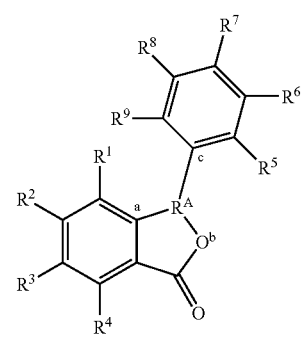

(I)

{in the formula (I), $R^1$, $R^2$, $R^3$, $R^4$, $R^5$, $R^6$, $R^7$, $R^8$ and $R^9$ may be the same or different, and represent hydrogen, halogen, hydroxy, alkoxy or alkyl; and $R^4$ represents the formula (II)

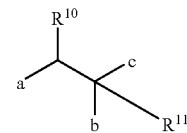

(II)

[in the formula (II), $R^{10}$ and $R^{11}$ may be the same or different, and represent hydrogen or halogen, or $R^{10}$ and $R^{11}$ together represent a binding] or the formula (III)

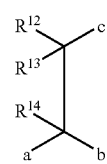

(III)

[in the formula (III), $R^{12}$ represents hydrogen, halogen, hydroxy, alkoxy, cyano or alkyl, $R^{13}$ and $R^{14}$ may be the same or different, and represent hydrogen or halogen, or $R^{13}$ and $R^{14}$ together represent a binding]} or a glycoside thereof or a pharmaceutically acceptable salt thereof.

9 Claims, No Drawings

LIVER FUNCTION PROTECTING OR AMELIORATING AGENT

TECHNICAL FIELD

The present invention relates to a liver function protecting or improving agent, a food and drink or a feed for protecting or improving liver functions, and an additive for foods and drinks or additives for feeds having liver function protecting or improving activity.

BACKGROUND OF THE INVENTION

The liver is an important organ which has various functions such as metabolic regulation and storage of sugar, protein and lipid which are three major nutrients, and decomposition and detoxification of substances unnecessary to the living body. These functions suffer acute or chronic disorders due to an excessive in take of alcohol, viral infection, bad eating habits, stress, smoking, etc. The advance of these disorders results in diseases such as acute hepatitis, chronic hepatitis, hepatic cirrhosis, alcoholic fatty liver, hepatitis B and liver cancer.

When liver cells are damaged by virus, alcohol, etc., enzymes such as aspartate aminotransferase (glutamic-oxaloacetic transaminase, hereinafter abbreviated as GOT) and alanine aminotransferase (glutamic-pyruvic transaminase, hereinafter abbreviated as GPT) in the cells leak into the blood, which raise the values indicating the activities of these enzymes. Accordingly, the levels of GOT and GPT activities in the blood are known as indices of the levels of the liver function disorders.

Known drugs used for the prevention or treatment of the liver function disorders include antiviral agents such as acyclovir, immunosuppressive agents, glutathione and the like. Foods and drinks which are recognized to be effective for protecting, strengthening and improving the liver functions include for example, turmeric, milk thistle, sesame lignan, oyster extract, liver extract and the like.

However, a strong need consistently exists for the development of pharmaceutical agents which are effective in prevention or treatment of liver diseases, and of health foods and drinks or animal feeds which enable prevention or treatment of hepatopathy by daily intake.

In connection with stilbenoid compounds, anti-allergic activities, anti-oxidative activities and anti-bacterial activities have been conventionally investigated on compounds isolated from *Hydrangeae Dulcis* Folium which is a herbal medicine [Summary of Lectures at the 2nd Symposium on Medicines and Foods, p. 85, 1999, Nihon Yakuyou Shokuhin Gakkai Zyunbi Iinkai (Japanese Society of Medicated Foods, Preparatory Committee)], and the like.

Reports have been made as follows on in vitro activities of the stilbenoid compounds.

In regard to the anti-allergic activities, it is reported that release of histamine from mast cells induced by compound 48/80 or calcium ionophore A23187 is suppressed by thunberginol A-G (50% inhibitory concentration: 9.4-92 µM), but is not suppressed by phyllodulcin or phyllodulcin 8-O-glucoside, hydrangenol, hydrangenol 8-O-glucoside, hydramacrophyllol A and B at 100 µM [Bioorganic & Medicinal Chemistry, 7, 1445 (1999)].

The extract of *Hydrangeae Dulcis* Folium (2000 mg/kg) is reported to suppress rat skin passive anaphylaxis through oral administration [Journal of the Pharmaceutical Society of Japan, 114(6), 401 (1994)]. In addition, it is reported that phyllodulcin 8-O-glucoside (300 and 500 mg/kg), hydrangenol (500 mg/kg), hydrangenol 8-O-glucoside (300 and 500 mg/kg), thunberginol A (300 and 500 mg/kg), thunberginol F (300 and 500 mg/kg) suppress rat skin passive anaphylaxis through oral administration, but phyllodulcin (300 and 500 mg/kg) does not suppress rat skin passive anaphylatic reaction [Biological & Pharmaceutical Bulletin, 22(8), 870 (1999)].

In connection with the anti-oxidative activities, it is reported that: as to DPPH (1,1-Diphenyl 2-Picrylhydrazyl) radical capturing capacity, the extract of *Hydrangeae Dulcis* Folium exhibits 50% capturing action at 0.099 mg, while phyllodulcin exhibits this activity at 0.208 mg, and hydrangenol at 1.074 mg; as to linoleic acid oxidation (iron rhodanate method), phyllodulcin exhibits more potent suppressive activity than $\alpha$-tocopherol or BHA (Butylated Hydroxyanisole), while hydrangenol exhibits a weak suppressive activity thereto; and as to NADP (Nicotinamide Adenine Dinucleotide Phosphate) H dependent lipid peroxidation in rat liver microsome, phyllodulcin exhibits a suppressive activity at a similar level to $\alpha$-tocopherol, while hydrangenol exhibits a weak suppressive activity thereto [Natural Medicine, 49(1), 84(1995)].

In regard to anti-bacterial activity, it is reported that phyllodulcin at 1000 ppm exhibits a proliferation suppressive activity on *Staphylococcus aureus* and *Staphylococcus epidemidis* (Japanese Published Unexamined Patent Application No. 43460/93), and phyllodulcin and hydrangenol exhibit an anti-bacterial activity on *Bacteroides melaninogenicus* and *Fusobacterium nucleatum* with the minimum growth inhibitory concentration of 1.25-2.5 ppm (Japanese Published Unexamined Patent Application No. 92829/94).

In regard to differentiation-inducing activity on leukocyte [Chemical & Pharmaceutical Bulletin, 48(4), 566 (2000)], isocoumarins such as thunberginol A (active at 100 µM) are reported to have more potent activity in vitro than dihydroisocoumarin such as phyllodulcin or hydrangenol (active at 300 µM). In addition, hydrangenol is reported to have a hyaluronidase inhibitory activity [Planta Medica, 54, 385 (1988)].

Moreover, it is reported that the extract of *Hydrangeae Dulcis* Folium (500 mg/kg) exhibits a cholagogic activity in an in vitro test, however, phyllodulcin (200 mg/kg) and hydrangenol (200 mg/kg) do not exhibit this activity [Journal of the Pharmaceutical Society of Japan, 114(6), 401 (1994)].

Furthermore, it is reported that the extract of *Hydrangeae Dulcis* Folium (200 and 400 mg/kg, oral administration) suppresses rat gastric ulcer induced by ethanol hydrochloride, however, phyllodulcin (75 mg/kg, oral administration) and hydrangenol (75 mg/kg, oral administration) do not suppress the ulcer [Journal of the Pharmaceutical Society of Japan, 114(6), 401 (1994)]

DISCLOSURE OF THE INVENTION

An object of the present invention is to provide a liver function protecting or improving agent, a food and drink or a feed for protecting or improving liver functions, and an additive for foods and drinks or an additive for feeds for protecting or improving liver functions.

The present invention relates to the following (1) to (15).

(1) A liver function protecting or improving agent which comprises a compound represented by the formula (I)

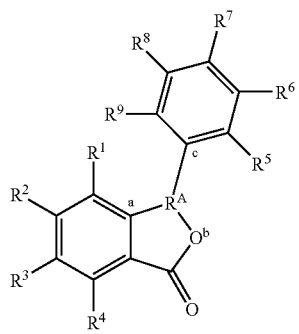

{in the formula (I), $R^1$, $R^2$, $R^3$, $R^4$, $R^5$, $R^6$, $R^7$, $R^8$ and $R^9$ may be the same or different, and represent hydrogen, halogen, hydroxy, alkoxy or alkyl; and $R^A$ represents the formula (II)

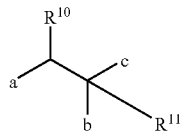

[in the formula (II), $R^{10}$ and $R^{11}$ may be the same or different, and represent hydrogen or halogen, or $R^{10}$ and $R^{11}$ together represent a binding] or the formula (III)

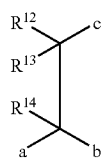

[in the formula (III), $R^{12}$ represents hydrogen, halogen, hydroxy, alkoxy, cyano or alkyl, $R^{13}$ and $R^{14}$ may be the same or different, and represent hydrogen or halogen, or $R^{13}$ and $R^{14}$ together represent a binding]} or a glycoside thereof [hereinafter referred to as compound (I)] or a pharmaceutically acceptable salt thereof.

(2) The liver function protecting or improving agent according to (1), wherein $R^1$, $R^3$, $R^5$, $R^8$ and $R^9$ represent hydrogen.

(3) The liver function protecting or improving agent according to (1) or (2), wherein $R^2$ represents hydrogen or hydroxy, $R^4$ represents hydroxy, $R^6$ and $R^7$ may be the same or different, and represent hydrogen, hydroxy or alkoxy.

(4) The liver function protecting or improving agent according to any one of (1) to (3), wherein $R^A$ represents the formula (II).

(5) The liver function protecting or improving agent according to any one of (1) to (3), wherein $R^A$ represents the formula (III).

(6) The liver function protecting or improving agent according to (1), wherein the compound (I) is phyllodulcin.

(7) The liver function protecting or improving agent according to (1), wherein the compound (I) is hydrangenol.

(8) A food and drink in which the liver function protecting or improving agent according to any one of (1) to (7) is added.

(9) A feed in which the liver function protecting or improving agent according to any one of (1) to (7) is added.

(10) An additive for foods and drinks in which the liver function protecting or improving agent according to any one of (1) to (7) is added.

(11) A feed additive in which the liver function protecting or improving agent according to any one of (1) to (7) is added.

(12) The liver function protecting or improving agent according to anyone of (1) to (7), which is administered orally.

(13) The liver function protecting or improving agent according to any one of (1) to (7), wherein the liver function is a function affected by an alcohol.

(14) A method for protecting or improving a liver function which comprises administering a therapeutically effective amount of the compound (I) or a pharmaceutically acceptable salt thereof to an animal including human.

(15) Use of the compound (I) or a pharmaceutically acceptable salt thereof for manufacturing a liver function protecting or improving agent.

In the definition of each group in the compound (I), the alkyl moiety of the alkyl and alkoxy may be for example, straight chain or branched alkyl having 1 to 10 carbon atoms, more preferably having 1 to 6 carbon atoms. More specifically, examples include methyl, ethyl, propyl, isopropyl, butyl, isobutyl, sec-butyl, tert-butyl, pentyl, neopentyl, hexyl, heptyl, octyl, nonyl, decyl and the like. Halogen represents each atom of fluorine, chlorine, bromine or iodine.

Kind and the chain length of the sugar that constitutes the glycoside are not particularly limited. Examples of the kind of the sugar include pentose, hexose, heptose and the like, and hexose is preferred. Examples of pentose include D-xylose, L-arabinose, D-arabinose, D-ribulose, D-xylulose, L-xylulose, D-ribose, D-deoxyribose and the like. Examples of hexose include D-glucose, D-fructose, D-mannose, D-galactose, L-galactose, D-tagatose, L-sorbose, L-fucose, D-fucose, D-quinovose, L-rhamnose and the like. Examples of heptose include sedoheptulose, persulose and the like.

The chain length of the sugar is for example, 1 to 10, preferably 1 to 6, and more preferably 1 to 3.

Examples of the pharmaceutically acceptable salt of the compound (I) include salts with for example, inorganic acids (e.g., hydrochloric acid, sulfuric acid, nitric acid and the like), organic acids (e.g., carbonic acid, bicarbonic acid, succinic acid, acetic acid, propionic acid, trifluoroacetic acid and the like), inorganic bases (e.g., alkali metals such as sodium or potassium, alkaline earth metals such as calcium or magnesium, and the like) and organic base compounds (e.g., organic amines such as triethylamine, basic amino acids such as arginine, and the like), and the like.

Examples of the compound (I) include compounds represented by the formula (IV)

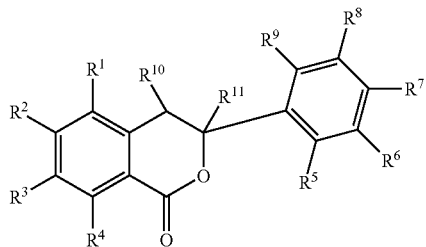

[in the formula (IV), $R^1$, $R^2$, $R^3$, $R^4$, $R^5$, $R^6$, $R^7$, $R^8$, $R^9$, $R^{10}$ and $R^{11}$ each are as defined previously] or glycosides thereof, or compounds represented by the formula (V)

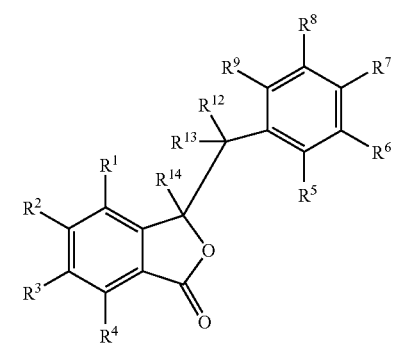

[in the formula (V), $R^1$, $R^2$, $R^3$, $R^4$, $R^5$, $R^6$, $R^7$, $R^8$, $R^9$, $R^{12}$, $R^{13}$ and $R^{14}$ each are as defined previously] or glycosides thereof.

In the formula (I), formula (IV) and formula (V), $R^1$, $R^3$, $R^5$, $R^8$ and $R^9$ are preferably hydrogen. Furthermore, in the formula (I), formula (IV) and formula (V), $R^2$ is preferably hydrogen or hydroxy, $R^4$ is preferably hydroxy, $R^6$ and $R^7$ are the same or different, and are preferably hydrogen, hydroxy, or alkoxy.

Specific examples of the compound (I) include phyllodulcin, hydrangenol, thunberginol A, phyllodulcin 8-O-glucoside, phyllodulcin 3'-O-glucoside, hydrangenol 8-O-glucoside, hydrangenol 4'-O-glucoside, 3-(fluorophenyl)-3,4-dihydroisocoumarin, 3-(fluorophenyl)isocoumarin, 3-(3',5'-dimethyl-4'-hydroxybenzylidene)phthalide, 4,5,6,7-tetraiodo-3-benzalphthalide, 4,5,6,7-tetraiodo-3-(α-cyanobenzal)phthalide, 8-methoxy-3-(p-methoxyphenyl)isocoumarin, 3,4-dihydro-3-(p-methoxyphenyl)isocoumarin, 5-chloro-8-hydroxy-6-methoxy-3-phenylisocoumarin and the like. These structures are show in Table 1.

TABLE 1

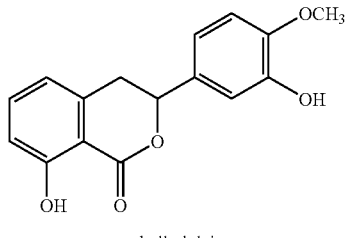

phyllodulcin

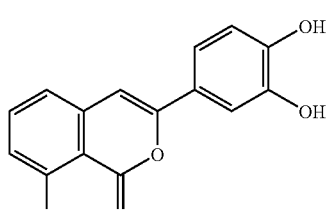

hydrangenol

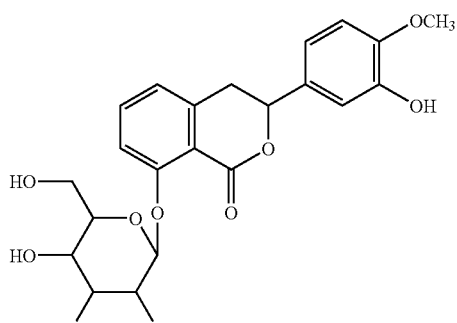

thunberginal A

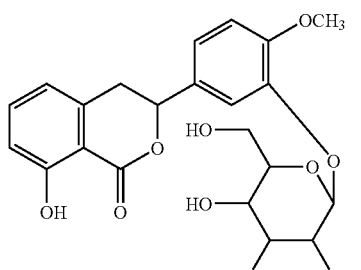

phyllodulcin 8-O-glucoside phyllodulcin 3'-O-glucoside

TABLE 1-continued

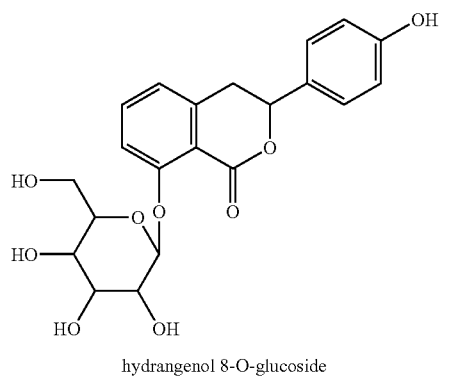

hydrangenol 8-O-glucoside

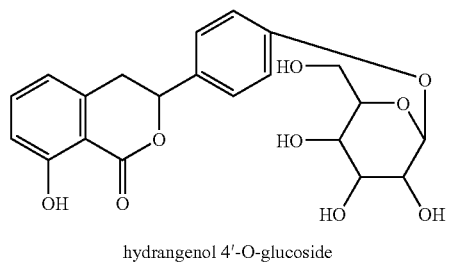

hydrangenol 4'-O-glucoside

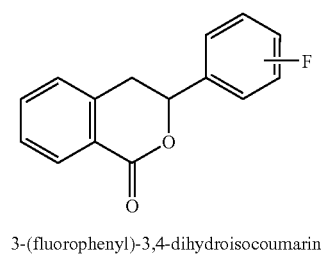

3-(fluorophenyl)-3,4-dihydroisocoumarin

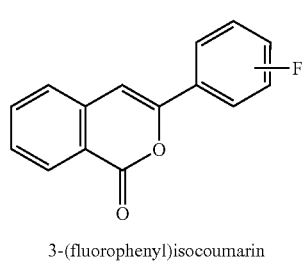

3-(fluorophenyl)isocoumarin

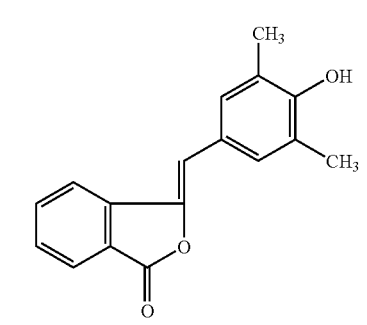

3-(3',5'-dimethyl-4'-hydroxybenzylidene)phtalide

TABLE 1-continued

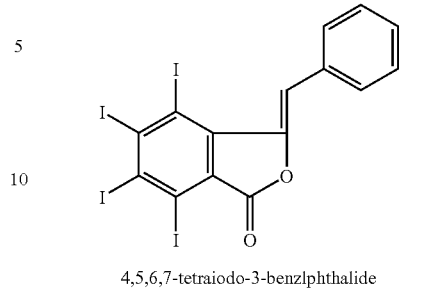

4,5,6,7-tetraiodo-3-benzlphthalide

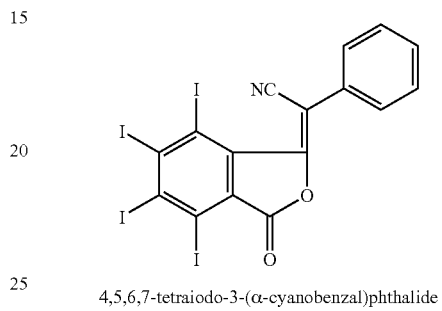

4,5,6,7-tetraiodo-3-(α-cyanobenzal)phthalide

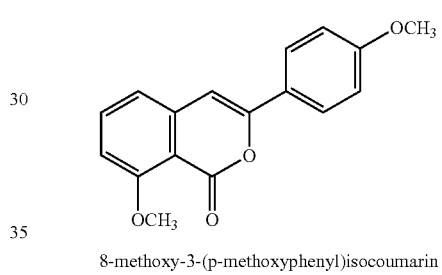

8-methoxy-3-(p-methoxyphenyl)isocoumarin

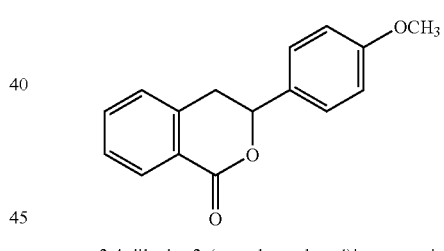

3,4-dihydro-3-(p-methoxyphenyl)isocoumarin

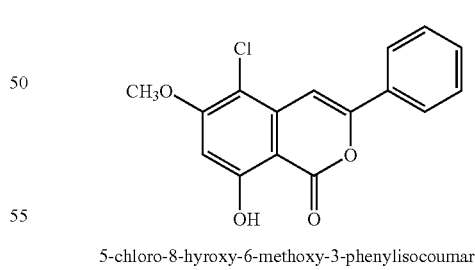

5-chloro-8-hyroxy-6-methoxy-3-phenylisocoumarin

The compound (I) or a pharmaceutically acceptable salt thereof may be chemically synthesized, or may be isolated and purified from a natural product which originally contains the compound (I) or a pharmaceutically acceptable salt thereof.

Illustrative examples of the process for chemically synthesizing the compound (I) or a pharmaceutically acceptable salt thereof include the following processes.

An analogy process to biosynthesis in which 3-(3-benzyloxy-4-methoxyphenyl)-2-propenal is used as a starting material [Chemical & Pharmaceutical Bulletin, 28(10), 3013 (1980)].

A process in which synthon-1-(3-benzyloxy-4-methoxyphenyl)-5-dimethylamino-1, 4-pentadiene-3-one and dimethyl 3-oxoglutarate are used as starting materials followed by aromatic anelation and debenzylation [Chemical & Pharmaceutical Bulletin, 31(12), 4360 (1983)].

A process in which N,N-diethyl-2-methylbenzamide is subjected to lithiumization followed by condensation with an aromatic aldehyde to subject to basic hydrolysis [Journal of Organic Chemistry, 49(5), 742 (1984)]. A process in which copper chloride is used as a catalyst and a site-directed oxidative lactonising reaction is applied [Chemical & Pharmaceutical Bulletin, 44(10), 1890 (1996)].

A process starting from the treatment of orthotoluic acid with excess amount of lithium isopropylamide [Synthetic Communications, 26(9), 1753 (1996)].

A process in which orthotoluate is treated with lithium isopropylamide to give an anion followed by polymerization [Synthesis, 1, 72 (1980)]. A process in which a homophthalic acid derivative is heated with an aromatic acyl chloride followed by subjecting to alkaline decomposition [Chemical & Pharmaceutical Bulletin, 29(9), 2491 (1981)].

A process in which homophthalic acid and benzoylchloride bromide are used as starting materials then alkaline hydrolyzed and via reduced racemic hydroxy acid [Indian Journal of Heterocyclic Chemistry, 8, 99 (1998)].

A process achieved by heating benzocyclobutenone with alcohol [Tetrahedron Letters, 38(33), 5745 (1997)]. A process in which a reaction between 4,5,6,7-tetraiodophthalic anhydride and phenyl acetate is executed [Egypt Journal of Chemistry, 22(2), 135 (1979)].

A process in which 3,4-dimethoxyphenyl acetate and phthalic anhydride are heated in the presence of sodium acetate followed by lactonization, and further, hydrolysis is executed in the presence of aqueous tetrahydrofuran and tetrabutylammonium bromide [Journal of Organic Chemistry, 59(26), 8220 (1994)].

A process in which an alkylbenzoic acid derivative is cyclized with a palladium catalyst in the presence of benzoquinone [Chemical & Pharmaceutical Bulletin, 42(8), 1700 (1994)].

A process in which 3,5-disubstituted 4-hydroxybenzaldehyde, which was synthesized by treating 2,6-disubstituted phenol with hexamethylenetetramide and boric acid followed by hydrolysis with sulfuric acid, is used as a starting material to subject to Wittig reaction with phospholan generated from triphenylphosphonium bromide [European Journal of Medicinal Chemistry, 13(5), 425 (1978)].

Examples of the natural product which originally contains the compound (I) or a pharmaceutically acceptable salt thereof include plants and herbal medicines such as *Hydrangea macrophylla* Ser. var. *Thunbergii* MAKINO, *Hydrangea serrata* var. *Thunbergii* and *Hydrangeae Dulcis* Folium. Examples of the plant which contains hydrangenol include plants in genus hydrangea such as *Hydrangea macrophylla* Ser. and *Hydrangea macrophylla* Ser. var. *otaksa* Makino, *Dichroae radix* and the like. Improved plants so that plenty of compound (I) or a pharmaceutically acceptable salt thereof is included, or cultured plant tissues may also be used. The compound (I) or a pharmaceutically acceptable salt thereof is obtained from the extract of the plant body in the form of the sole material or the mixture.

For the purification from a natural product, a technique generally used in the purification of compounds having the lower molecular weight is employed in which the target compound is extracted using an organic solvent followed by a solvent fractionation method, a column chromatographic method, an HPLC method, a recrystallization method or the like.

Examples of the method of extraction include extraction with various solvents, supercritical fluid extraction and the like. Extracts may further be treated by various methods of solid-liquid separation such as sedimentation, cake filtration, clear filtration, centrifugal filtration, centrifugal sedimentation, separation by compression and filter press, various concentration methods, various drying methods, methods of making various preparations such as granulation and pulverization, various purification methods, and the like.

Examples of the purification method include solvent fractionation methods, column chromatographic methods, recrystallization methods and the like. Specifically preferred is column chromatographic method using various carriers such as DIAION HP-20 (manufactured by Mitsubishi Chemical Corporation) and Sephadex LH-20 (manufactured by Pharmacia).

Examples of the concentration and drying method include film drying methods such as freeze-drying, natural drying, hot air-drying, blow-drying, spray drying, drying under reduced pressure, sun-drying, vacuum drying, fluidized-bed drying, foam-bed drying and drum drying, drying methods such as ultrasonic drying and electromagnetic wave drying. Preferred are a spray drying method and a freeze-drying method.

In the step of extraction and treatment of an extract, an antioxidant, a preservative, etc. may be added.

As the solvent used in extraction with a solvent, any solvent which can extract the compound (I) or a pharmaceutically acceptable salt thereof can be used. Examples of the preferred solvent include aqueous media such as water, distilled water, deionized water, an aqueous solution of an inorganic salt and buffer, monovalent alcohols such as methanol, ethanol, propanol and butanol, polyvalent alcohols such as propylene glycol and glycerol, and organic solvents such as hexane, toluene, petroleum ether, benzene, ethyl acetate, chloroform, dichloromethane, 1,1,2-trichloroethene, dimethyl sulfoxide and acetone. Preferred are aqueous media and alcohols.

Examples of the buffer include phosphate buffer, citrate buffer and the like. Examples of the inorganic salt for the aqueous solution of an inorganic salt include sodium chloride, potassium chloride, calcium chloride and the like.

Preferred alcohols are monovalent alcohols and a preferred monovalent alcohol is ethanol.

These solvents can be used alone or as a mixture of multiple solvents. As the mixed solvent, water-containing alcohols are preferred. Water-containing monovalent alcohols are more preferred and water-containing ethanol is particularly preferred. The water content is preferably 70% or lower, and more preferably 40% or lower.

As the solvent, supercritical fluidized carbon dioxide may also be employed.

Extraction is conducted using the solvent in an amount of 0.1 part by weight to 10000 parts by weight, and preferably 1 part by weight to 100 parts by weight per 1 part by weight of a plant body. Although the temperature for extraction is not particularly limited, it is preferably 0° C. to 100° C., and more preferably 20° C. to 90° C. Although the time period for extraction is not particularly limited, it is preferably one minute to one week, and more preferably 30 minutes to one day.

Concentration of the extract may be conducted under either normal pressure or reduced pressure. Although the temperature for the concentration is also not particularly limited, it is preferably 40° C. or less. The compound (I) or a pharmaceutically acceptable salt thereof may be used in the form of a mixture of the extract, however, it may be also isolated as needed. The isolation can be performed through extraction with an organic solvent such as lower alkyl ketone, lower alcohol, lower fatty acid, lower fatty acid ester, lower aliphatic ether, halogen-substituted or unsubstituted lower hydrocarbon, or the like followed by subjecting the concentrate of this extract to column chromatography using silica gel, alumina or the like as a carrier.

Examples of the lower alkyl ketone include acetone, methylethylketone and the like. Examples of lower alcohol include methanol, ethanol and the like. Examples of the lower fatty acid include acetic acid and the like. Examples of the lower fatty acid ether include ethyl ether, isopropyl ether and the like. Examples of the halogen-substituted or unsubstituted lower hydrocarbon include chloroform, carbon tetrachloride, n-hexane and the like. These may be used alone or as a mixture.

In the present invention, protection of a liver function involves activities to protect the liver functions from various disorders, activities to prevent the liver functions from a disorder, and the like. Improvement of a liver function involves activities to recover or cure the disordered functions of liver, activities to improve or enhance liver function, and the like.

The term "liver function" as used herein means every function of the liver and there is no limit as to the definition of the term. Specific examples of the liver function include those relating to blood and circulation such as storage of blood (adjustment of the amount of circulating blood), treatment of blood pigments (discharge of hemoglobin), formation of bile, enterohepatic circulation of bile pigments, and synthesis of plasma proteins (e.g. acute phase proteins, albumin, blood coagulation factors, steroid-binding proteins and other hormone-binding proteins), metabolic functions such as metabolism of nutrients and vitamins (e.g. glucose and other sugars, amino acids, lipids-fatty acids, cholesterol, lipoproteins, lipid-soluble vitamins and water-soluble vitamins), detoxification or decomposition functions such as inactivation of various substances (e.g. alcohols, acetaldehyde, toxins, steroids such as estrogen and androsterone, and other hormones), immune functions ["Seirigaku Tenbo" (View of Physiology), 19th edition (Mar. 31, 2000), "Atarashii Rinsho Eiyogaku" (New Study of Clinical Nutrition), 3rd revision (May 20, 2000)], and the like. These functions all suffer damage from an alcohol.

The liver function protecting or improving agent of the present invention can improve a liver function disorder through the administration thereof to a human or an animal already having a disorder in liver function. Further, the liver function protecting or improving agent of the present invention can prevent a liver function disorder through the administration thereof to a human or an animal with no manifestation of a liver function disorder.

The liver function protecting or improving agent of the present invention contains the compound (I) or a pharmaceutically acceptable salt thereof, and may contain one or more pharmaceutically acceptable carriers as needed, as well as an active ingredient for the therapy as needed.

The liver function protecting or improving agent of the present invention is produced by mixing the compound (I) or a pharmaceutically acceptable salt thereof with a carrier as needed, according to an arbitrary method which is well known in the technical field of pharmaceutics.

It is desirable to employ the most effective route for administration of the formulation for treatment. Examples of suitable administration route include oral administration and parenteral administration such as intravenous administration, intraperitoneal administration and subcutaneous administration. Among these, oral administration is preferred.

Examples of dosage form for the administration include tablets, powders, granules, pills, suspensions, emulsions, infusa, capsules, syrups, injections, liquids, elixirs, extracts, tinctures, fluid extracts and the like.

Dosage forms suitable for oral administration for example, extracts, tinctures, fluid extracts and the like can be prepared by extracting the compound (I) or a pharmaceutically acceptable salt thereof from a body of e.g., a plant of the family Saxifragaceae with for example, water, ethanol or a mixture of water and ethanol, with or without the following concentration of the extract.

Liquid preparations suitable for oral administration such as syrups can be prepared using carriers such as water, sugars (e.g. sucrose, sorbitol and fructose), glycols (e.g. polyethylene glycol and propylene glycol), oils (e.g. sesame oil, olive oil and soybean oil), antiseptics (e.g. p-hydroxybenzoic acid esters), paraoxybenzoic acid derivatives (e.g. methyl paraoxybenzoate), preservatives (e.g. sodium benzoate) and flavors (e.g. strawberry flavor and peppermint).

Dosage forms suitable for oral administration for example, tablets, powders, granules and the like can be prepared using sugars such as lactose, white sugar, glucose, sucrose, mannitol and sorbitol, starch such as potato starch, wheat starch and corn starch, inorganic substances such as calcium carbonate, calcium sulfate, sodium bicarbonate and sodium chloride, excipients such as crystalline cellulose and plant powders (e.g. licorice powder and gentian powder), disintegrating agents such as starch, agar, gelatin powder, crystalline cellulose, carmellose sodium, carmellose calcium, calcium carbonate, sodium bicarbonate and sodium alginate, lubricants such as magnesium stearate, talc, hydrogenated vegetable oil, macrogol and silicone oil, binders such as polyvinyl alcohol, hydroxypropyl cellulose, methyl cellulose, ethyl cellulose, carmellose, gelatin and starch paste, surfactants such as fatty acid ester, plasticizers such as glycerin, and the like.

Preparations suitable for parenteral administration such as injections, preferably comprise a sterilized aqueous agent containing an active compound which is isotonic to the recipient's blood. In the case of an injection, for example, an injectable solution is prepared using a carrier such as a salt solution, a glucose solution, or a mixture of a salt solution and a glucose solution.

The antiseptics, preservatives, surfactants, etc. as described above can also be employed in such preparations for parenteral administration.

The dose and dosage frequency of the liver function protecting or improving agent of the invention will vary depending on the administration route, the age and body weight of a patient, and property or severity of the symptom to be treated, without specific restriction. In general, when orally administered to an adult, it is suitable to administer in an amount of 0.01 mg to 50 g, preferably 0.05 mg to 10 g in terms of the compound (I) or a pharmaceutically acceptable salt thereof once to several times per day. In the case of parenteral administration such as intravenous administration, it is suitable to administer to an adult in an amount of 0.001 mg to 50 g, preferably 0.01 mg to 10 g in terms of the compound (I) or a pharmaceutically acceptable salt thereof once to several times per day. In the case of administration to an animal, the dose and dosage frequency will vary depending on the age and kind of the animal, and the property or severity of the symptom, without specific restriction. In general, when orally administered, it is suitable to administer in an amount of 0.1 μg to 10 g, preferably 1 μg to 1 g per kg of body weight once to several times per day. In the case of parenteral administration such as intravenous administration, it is suitable to administer in an amount of 0.01 μg to 10 g, preferably 0.1 μg to 1 g per kg of body weight once to several times per day. However, the dose and dosage frequency may vary depending upon the above-mentioned various conditions.

The food and drink or the feed in which the compound (I) or a pharmaceutically acceptable salt thereof is added may include those prepared by adding the compound (I) or a pharmaceutically acceptable salt thereof to a food and drink or a feed which originally contains the compound (I) or a pharmaceutically acceptable salt thereof or which does not originally contain the compound (I) or a pharmaceutically acceptable salt thereof to produce in a process for producing ordinary foods and drinks or feeds. Further, the food and drink or the feed may be processed by a method of processing ordinary foods and drinks or feeds. Examples of the method of processing include granulating methods such as fluidized bed granulation, stirring granulation, extrusion granulation, rolling granulation, air stream granulation, compression molding granulation, disruption granulation, spray granulation and blasting granulation, coating methods such as pan coating, fluidized bed coating and dry coating, swelling methods such as puff drying, excess steam method, foam mat method and microwave heating method, and the like.

The food and drink or the feed containing the compound (I) or a pharmaceutically acceptable salt thereof or materials therefor are not particularly limited, which may include those comprising the compound (I) or a pharmaceutically acceptable salt thereof, and those which are not substantially comprising the compound (I) or a pharmaceutically acceptable salt thereof.

The liver function protecting or improving activity of the food and drink or the feed which comprises the compound (I) or a pharmaceutically acceptable salt thereof can be enhanced by adding thereto the compound (I) or a pharmaceutically acceptable salt thereof.

Although the amount of the compound (I) or a pharmaceutically acceptable salt thereof of the invention to be added to the food and drink or the feed is not particularly limited as long as it is an amount to give a content which enables the food and drink or the feed to exhibit liver function protecting or improving activity, the content of the compound (I) or a pharmaceutically acceptable salt thereof allowed in the food and drink or the feed is preferably 0.001 to 100%, more preferably 0.01 to 100%, and particularly preferably 0.1 to 100%.

Specific examples of the food and drink to which the compound (I) or a pharmaceutically acceptable salt thereof is added include juice, soft drinks, soup, tea, dairy products (e.g. lactic acid bacteria beverages, fermented milk, frozen dessert, butter, cheese, yogurt, processed milk and skim milk powder), meat products (e.g. ham, sausage and hamburger), fish cake products, egg products (e.g. fried or steamed foods made of beaten eggs), confectionery (e.g. cookies, jelly, snacks and chewing gum), bread, noodles, pickles, smoked foods, dry foods, preserved foods boiled in soy sauce, seasonings and the like.

The food and drink may be in any of the forms such as a powder food, a sheet-shaped food, a bottled food, a canned food, a retort pouched food, a capsule food, a tablet-shaped food, a liquid food and a health drink, and the like.

The food and drink of the present invention is used for the protection or improvement of liver function, as a health food and drink or a functional food and drink.

When the present food and drink for protecting or improving liver function which comprises the compound (I) or a pharmaceutically acceptable salt thereof as an active ingredient is ingested, the amount of intake is not particularly limited, however, it is 0.01 mg to 50 g, and preferably 0.05 mg to 10 g in terms of the weight of the compound (I) or a pharmaceutically acceptable salt thereof given to an adult per day. It is ingested in this amount of intake for 1 day to 1 year, and preferably for 2 weeks to 3 months. However, this amount of intake is merely a typical example, and can be appropriately adjusted to fall within a suitable range according to the recipient's extent of the symptom, age, weight, etc.

Examples of the feed to which the compound (I) or a pharmaceutically acceptable salt thereof is added include feeds for animals such as mammals, birds, reptiles, amphibians and fish. Specific examples of the feed include feeds for pets such as dogs, cats and mice, feeds for livestock such as cows and pigs, feeds for poultry such as hens and turkeys, feeds for cultivated fish such as sea breams and young yellowtails, and the like.

The feed of the present invention can be produced by appropriately mixing the compound (I) or a pharmaceutically acceptable salt thereof with a feed material.

Exemplary feed materials include grains, bran, vegetable oil cakes, animal feed materials, other feed materials, purified products and the like.

Examples of the grain include milo, wheat, barley, oats, rye, nonglutinous brown rice, buckwheat, foxtail millet, broomcorn millet, Japanese millet, corn, soybean and the like.

Examples of the bran include rice bran, defatted rice bran, wheat bran, wheat middlings, wheat germ, barley bran, pellet, corn bran, corn germ and the like.

Examples of the vegetable oil cake include soybean oil cake, soybean flower, linseed oil cake, cottonseed oil cake, peanut oil cake, safflower oil cake, coconut oil cake, palm oil cake, sesame oil cake, sunflower oil cake, rapeseed oil cake, kapok oil cake, mustard seed oil cake and the like.

Examples of the animal feed material include fish meal (e.g. northern ocean meal, imported meal, whole meal and coastal meal), fish soluble, meat meal, meat and bone meal, blood powder, degraded hair, bone meal, treated by-products for livestock, feather meal, silkworm pupa, skim milk powder, casein, dry whey and the like.

Examples of other feed material include stalks and leaves of plants (e.g. alfalfa, hay cube, alfalfa leaf meal and powder of false acacia), processed industrial by-products of corn (e.g. corn gluten, meal, corn gluten feed and corn steep liquor), processed starch products (e.g. starch), sugar, fermentation industrial products (e.g. yeast, beer cake, malt root, alcohol cake and soy sauce cake), agricultural by-products (e.g. processed citrus fruit cake, tofu cake, coffee cake and cocoa cake) and others (e.g. cassava, broad bean, guar meal, seaweeds krill, spirulina, chlorella and minerals) and the like.

Examples of the purified product include proteins (e.g. casein and albumin), amino acids, carbohydrates (e.g. starch, cellulose, sucrose and glucose), minerals, vitamins and the like.

When the feed to which the compound (I) or a pharmaceutically acceptable salt thereof is added is fed to an animal, the amount of intake is not particularly limited, however, it is 0.1 μg to 10 g, and preferably 0.1 μg to 1 g in terms of the weight of the compound (I) or a pharmaceutically acceptable salt thereof per kg of the body weight of the animal per day. It is ingested in this amount of intake for 1 day to 1 year, and preferably for 2 weeks to 3 months. However, this amount of intake is merely a typical example, and can be appropriately adjusted to fall within a suitable range according to the kind, age, body weight, etc. of an animal to be fed.

The additive for foods and drinks or feeds in which the compound (I) or a pharmaceutically acceptable salt thereof is added may be prepared by adding the compound (I) or a pharmaceutically acceptable salt thereof to an additive for foods and drinks or feeds, optionally followed by adding an additive generally employed in foods and drinks or feeds as needed, for example, additives listed in Food Additives Indication Pocket Book (Japan Food Additives Association, Jan. 6, 1997) such as sweeteners, coloring agents, preservatives, thickening stabilizers, antioxidants, color developing agents bleaching agents, fungicides, gum bases, bitter agents, enzymes or enzyme sources, gloss agents, sour agents, seasonings, emulsifiers, fortifier dietary supplements, additional materials for preparation, flavors, spice extracts and the like. Moreover, the carriers illustrated in the above description of the liver function protecting or improving agent may also be added.

Although concentration of the compound (I) or a pharmaceutically acceptable salt thereof in the additive for foods and drinks or feeds is not particularly limited, it is preferably 1 to 99%, more preferably 10 to 90%, particularly preferably 20 to 80%.

Examples of the sweetener include aspartame, licorice, stevia, xylose and *Momordica grosvenori* and the like.

Examples of the coloring agent include carotenoid, turmeric pigment, flavonoid, caramel pigment, oriental gromurell pigment, spirulina pigment, chlorophyll, red sweet potato pigment, red Chinese yam pigment, perilla pigment, blueberry pigment and the like.

Examples of the preservative include sodium sulfite, benzoic acid and benzoates, extract of *Aralia cordata*, Japanese Styrax benzoin extract, Rumpet roman extract, sorbic acid and sorbates, propionic acid and propionates, and the like.

Examples of the thickening stabilizer include gums such as gum arabic and xanthane gum, alginic acid and alginates, chitin, chitosan, aloe extract, guar gum, hydroxypropyl cellulose, casein sodium, cornstarch, carboxymethylcellulose, gelatin, agar, dextrin, methyl cellulose, polyvinyl alcohol, microfibrous cellulose, microcrystalline cellulose, seaweed cellulose, sodium polyacrylate, sodium polyphosphate, carrageenan, yeast cell wall, extract of konjac, nata de coco, mannan and the like.

Examples of the antioxidant include vitamin C, sodium ethylenediaminetetraacetate, calcium ethylenediaminetetraacetate, erythorbic acid, oryzanol, catechin, quercetin, clove extract, enzyme-treated rutin, apple extract, sesame oil extract, dibutylhydroxytoluene, fennel extract, horseradish extract, water dropwort extract, tea extract, Tempeh extract, extract of *Houttuynia cordata*, tocotrienol, tocopherols, rapeseed oil extract, green coffee extract, sunflower seed, ferulic acid, butylhydroxyanisole, blueberry leaf extract, propolis extract, hego-ginkgo leave extract, hesperetin, pepper extract, garden balsam extract, gallic acid, myrica extract, eucalyptus extract, rosemary extract and the like.

Examples of the color developing agent include sodium nitrite and the like, and examples of the bleaching agent include sodium sulfite and the like.

Examples of the fungicide include orthophenylphenol and the like.

Examples of the gum base include methyl acetylricinoleate, Japanese lacquer wax, ester gum, elemi resin, urucury wax, ozokerite, opopanax resin, kauri gum, carnauba wax, guaiacum resin, gutta katiau, gutta hangkang, gutta percha, glycerin fatty acid ester, spermaceti wax, copaiba balsam, copal resin, gum, rice bran wax, sugar cane wax, shellac, jelutong, sucrose fatty acid ester, sorba, sorbitan fatty acid ester, talc, calcium carbonate, dammar resin, chicle, chilte, tunu, low molecular weight gum, paraffin wax, fir balsam, propylene glycol fatty acid ester, powdered pulp, powdered rice husks, jojoba wax, polyisobutylene, polybutene, microcrystalline wax, mastic, massaranduba chocolate, beeswax, calcium phosphate and the like.

Examples of the bitter agent include isoalpha bitter acid, caffeine, kawaratake extract, cinchona extract, Amur cork extract, gentian extract, spice extracts, enzyme-treated naringin, Jamaica quassia extract, theobromine, naringin, bitter ash extract, warmwood extract, isodonis extract, himematsutake extract, borapet, methyl thioadenosine, litchi extract, olive tea, sour orange extract, hop extract, mugwort extract and the like.

Examples of the enzyme or enzyme source include amylase, trypsin, rennet, lactic acid bacteria and the like.

Examples of the gloss agent include Japanese lacquer wax, vegetable wax and the like.

Examples of the sour agent are adipic acid, itaconic acid, citric acid and citrates, succinic acid and succinates, sodium acetate, tartaric acid and tartrates, carbon dioxide, lactic acid, phytic acid, fumaric acid, malic acid, phosphoric acid and the like.

Examples of the seasoning include amino acids such as asparagine, aspartic acids, glutamic acid, glutamine, alanine, isoleucine, glycine, serine, cystine, tyrosine, leucine and proline, nucleic acids such as sodium inosinate, sodium uridylate, sodium guanylate, sodium cytidylate, calcium ribonucleotide and sodium ribonucleotide, organic acids such as citric acid and succinic acid, potassium chloride, sodium solution of low salt content prepared from salt lake water, crude potassium chloride from sea water, whey salt, tripotassium phosphate, dipotassium hydrogenphosphate, potassium dihydrogenphosphate, disodium hydrogenphosphate, sodium dihydrogenphosphate, trisodium phosphate, chlorella extract and the like.

Examples of the emulsifier include fatty acid monoglyceride, sorbitan fatty acid ester and the like.

Examples of the fortifier dietary supplement include zinc salts, vitamin C, various amino acids, 5-adenylic acid, iron chloride, hesperidin, various kinds of burnt calcium, various kinds of unburnt calcium, dibenzoylthiamine, calcium hydroxide, calcium carbonate, thiamine hydrochloride, dunaliella carotene, tocopherol, nicotinic acid, carrot carotene, palm oil carotene, calcium pantothenate, vitamin A, hydroxyproline, calcium dihydrogenpyrophosphate, iron (II) pyrophosphate, iron (III) pyrophosphate, ferritin, heme iron, menaquinone, folic acid, riboflavin and the like.

Examples of the additional material for preparation include processing aids such as acetone and ion exchange resin, extract of fig leaf, extract of rice straw ash, kaolin, glycerin fatty acid ester, mulberry extract, bone ash, perilla extract, ginger extract, various tannins, Phaffia color extract, grape seed extract, ethanol and the like.

Examples of the flavor include strawberry flavor, peppermint flavor and the like.

Examples of the spice extract include chili pepper extract, garlic extract and the like.

The present invention is hereinafter explained in detail according to Examples. However, the Examples described below should not be construed as limiting the invention. Equipments used in the Examples are as those described below.

Mass spectrometer (device: JMS-HX110/110A (JEOL, Ltd.), FAB gas: Xe, charged voltage: 10 kV, matrix: m-NBA), high resolution FAB mass spectrum (positive mode; matrix: m-NBA): nuclear magnetism resonance method (device: JNM-A400 (JEOL, $^1$H-NMR: 400 MHz, $^{13}$C-NMR: 100 MHz).

BEST MODE FOR CARRYING OUT THE INVENTION

EXAMPLE 1

Isolation of Phyllodulcin

Dry powder of *Hydrangeae Dulcis* Folium (manufactured by Shihira Shoten) in an amount of 1.0 kg was extracted twice with 20 L of methanol at room temperature through leaving to stand for 2 days. Thus obtained extract was concentrated and evaporated to dryness to obtain 425.8 g of a methanol extract. The extract was subjected to fractionation using 6 L of a silica gel column (Wako gel C-300, manufactured by Wako Pure Chemical Industries, Ltd.) by a 10% stepwise method starting from n-hexane to AMC solution (referring to a chloroform solution containing 0.1% acetic acid and 0.5% of methanol).

Thus eluted 90% AMC solution-containing n-hexane fraction and 100% AMC solution fraction (each fraction of 6 L) were mixed to obtain a fraction I.

The fraction I was concentrated followed by subjecting to fractionation using 2 L of a silica gel column (Wako gel C-300, manufactured by Wako Pure Chemical Industries, Ltd.) by a 10% stepwise method starting from n-hexane to acetone to obtain 50%, 60% and 70% acetone-containing n-hexane fractions (each fraction of 2 L). The three fractions were combined and concentrated, and thus 26.2 g of phyllodulcin powder was obtained by a recrystallization process.

The values of $^1$H-NMR and $^{13}$C-NMR of the isolated compound each agreed with values of $^1$H-NMR and $^{13}$C-NMR of an authentic sample.

EXAMPLE 2

Isolation of Hydrangenol

Dry powder of *Hydrangeae Dulcis* Folium (manufactured by Shihira Shoten) in an amount of 1.0 kg was extracted twice with 20 L of methanol at room temperature through leaving to stand for 2 days. Thus obtained extract was concentrated and evaporated to dryness to obtain 425.8 g of a methanol extract. The extract was subjected to fractionation using 6 L of a silica gel column (Wako gel C-300, manufactured by Wako Pure Chemical Industries, Ltd.) by a 10% stepwise method starting from n-hexane to AMC solution, and then a 0.5% stepwise method starting from chloroform to methanol.

Thus eluted 1.0% methanol-containing chloroform fraction (6 L) was combined to give a fraction II.

The fraction II was concentrated followed by subjecting to fractionation using 400 mL of a normal phase column (LiChroprep Si60, manufactured by Merck & Co., Inc.) by a 20% stepwise method starting from n-hexane to AMC solution, and then a 1.0% stepwise method starting from chloroform to methanol to obtain 60%, 80% and 100% AMC solution-containing n-hexane fractions and a 1.0% methanol-containing chloroform fraction (each fraction of 2.4 L). The four fractions were combined and concentrated, and thereafter subjected to fractionation using 2 L of a silica gel column (Wako gel C-300) by a 5% stepwise method starting from toluene to ethyl acetate to obtain toluene fractions (each fraction of 2 L) each containing 15%, 20% and 25% ethyl acetate. The three fractions were combined and concentrated, and thus 18.4 g of hydrangenol powder was obtained by a recrystallization process.

Values of $^1$H-NMR spectrum [400 MHz, heavy DMSO solution, 30° C.] and $^{13}$C-NMR spectrum [100 MHz, heavy DMSO solution, 30° C.] of the isolated hydrangenol agreed with values for hydrangenol in the literatures [$^1$H-NMR: Agricultural Chemistry (Nougei Kagaku) Vol. 47, No. 10, page 605, 1973, and $^{13}$C-NMR: Chemical & Pharmaceutical Bulletin, 44(8), 1440 (1996)].

EXAMPLE 3

Isolation of Thunberginol A

Dry powder of *Hydrangeae Dulcis* Folium (manufactured by Shihira Shoten) in an amount of 1.0 kg was extracted twice with 20 L of methanol at room temperature through leaving to stand for 2 days. Thus obtained extract was concentrated and evaporated to dryness to obtain 425.8 g of a methanol extract. The extract was subjected to fractionation using 6 L of a silica gel column (Wako gel C-300, manufactured by Wako Pure Chemical Industries, Ltd.) by a 10% stepwise method starting from n-hexane to AMC solution, and then a 0.5% stepwise method starting from chloroform to methanol.

Thus eluted 2.0% and 2.5% methanol-containing chloroform fractions (each fraction of 6 L) were combined to give a fraction III.

The fraction III was concentrated followed by subjecting to fractionation using 2 L of a silica gel column (Wako gel C-300, manufactured by Wako Pure Chemical Industries, Ltd.) by a 10% stepwise method starting from n-hexane to acetone to obtain a 50% acetone-containing n-hexane fraction (2 L). The fraction was concentrated followed by subjecting to fractionation using 100 mL of a normal phase column (LiChroprep Si60, manufactured by Merck & Co., Inc.) by a 5% stepwise method starting from toluene to ethyl acetate to obtain toluene fractions (each fraction of 600 mL) each containing 10%, 15% and 20% ethyl acetate. The three fractions were combined and concentrated followed by subjecting to fractionation using 100 mL of a reverse phase column (Cosmosil140C$_{18}$OPN, manufactured by Nacalai Tesque, Inc.) by a 10% stepwise method starting from water to methanol to obtain 50%, 60% and 70% methanol-containing water fractions (each fraction of 600 ml). The three fractions were combined and concentrated, and thus 0.6 g of thunberginol A was obtained by a recrystallization process.

Values of $^1$H-NMR spectrum [400 MHz, heavy DMSO solution, 30° C.] and $^{13}$C-NMR spectrum [100 MHz, heavy DMSO solution, 30° C.] of the isolated thunberginol A agreed well with values in the literatures [Chem. Pharm. Bull., 42(11), 2225 (1994)].

EXAMPLE 4

Production of a Feed Containing Phyllodulcin at a Concentration of 0.366%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 39.734 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 1 | 0.366 wt % |

EXAMPLE 5

Production of a Feed Containing Phyllodulcin at a Concentration of 0.122%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 39.978 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 1 | 0.122 wt % |

EXAMPLE 6

Production of a Feed Containing Phyllodulcin at a Concentration of 0.0366%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.0634 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 1 | 0.0366 wt % |

EXAMPLE 7

Production of a Feed Containing Hydrangenol at a Concentration of 0.324%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 39.776 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 2 | 0.324 wt % |

EXAMPLE 8

Production of a Feed Containing Hydrangenol at a Concentration of 0.108%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 39.992 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 2 | 0.108 wt % |

EXAMPLE 9

Production of a Feed Containing Hydrangenol at a Concentration of 0.0324%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.0676 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 2 | 0.0324 wt % |

EXAMPLE 10

Production of a Feed Containing Thunberginol A at a Concentration of 0.039%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.061 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 3 | 0.039 wt % |

EXAMPLE 11

Production of a Feed Containing Thunberginol A at a Concentration of 0.013%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.087 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 3 | 0.013 wt % |

EXAMPLE 12

Production of a Feed Containing Thunberginol A at a Concentration of 0.0039%

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.0961 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |
| Powder produced in Example 3 | 0.0039 wt % |

COMPARATIVE EXAMPLE 1

Following materials were admixed to produce a feed.

| | |
|---|---|
| Sucrose (Kishida Chemical Co., Ltd.) | 20.0 wt % |
| Corn oil (Nacalai Tesque, Inc.) | 5.0 wt % |
| Choline bitartrate (Tokyo Kasei Kogyo Co., Ltd.) | 0.4 wt % |
| Corn starch (Nippon Starch Chemical Co., Ltd.) | 40.1 wt % |
| AIN-76 vitamin (Oriental Yeast Co., Ltd.) | 1.0 wt % |
| AIN-76 mineral (Oriental Yeast Co., Ltd.) | 3.5 wt % |
| Cellulose (Oriental Yeast Co., Ltd.) | 5.0 wt % |
| Casein (Wako Pure Chemical Industries, Ltd.) | 25.0 wt % |

EXAMPLE 13

Suppression of Galactosamine-induced Rat Hepatopathy by Phyllodulcin and Hydrangenol.

Male Wistar white rats (150±20 g, purchased from Japan SLC) were kept for at least 3 days under a fixed condition (temperature: 24±2° C., humidity: 60±5%, light and dark interval: 12 hours) for adaptation, and then fed respectively with the feeds produced in Examples 4-8 and the feed produced in Comparative Example 1 for 15 days. On the 14th day, 350 mg/kg of galactosamine (dissolved in physiological saline at a concentration of 35 mg/ml, and adjusted to pH 7.1) was intraperitoneally administered to each rat. Twenty-two hours after the administration of galactosamine, each of the rats was subjected to laparotomy under anesthesia with Nembutal and blood was collected.

Using thus obtained blood samples, blood GPT activity was measured as an indication of a liver function in the following manner. The collected blood was coagulated and separated by centrifugation to obtain a serum. The GPT level in the serum was measured using Fuji Drychem System 3500 (manufactured by Fuji Photo Film Co., Ltd.) with thus obtained serum. The GPT activity of each test group was calculated as the relative value (%) from the value obtained for each Example based on the value obtained for the feed in Comparative Example 1 expressed as 100%. The value is expressed in terms of average value±standard error and the statistical test of significance was carried out by Student's T-test.

The results are shown in Table 2.

TABLE 2

| Active ingredient | Feed | Concentration (%) | GPT activity (%) | Test of significance |
|---|---|---|---|---|
| phyllodulcin | Example 4 | 0.366 | 11.8 ± 18.0 | p = 0.0002 |
| | Example 5 | 0.122 | 54.7 ± 32.2 | p = 0.0400 |
| | Example 6 | 0.037 | 52.7 ± 59.9 | p = 0.1241 |
| hydrangenol | Example 7 | 0.324 | 64.6 ± 116.5 | p = 0.5177 |
| | Example 8 | 0.108 | 27.8 ± 45.4 | p = 0.0343 |

When the feeds of Examples 4-8 were administered, the GPT activity in serum which is an indication of a liver function disorder was kept low in comparison with the case in which the feed of Comparative Example was administered. It is revealed that hepatopathy was suppressed accordingly.

During 15 days of the feeding, there was no difference in weight increase among the cases where any of the feeds was given, and no abnormality was also recognized in appearance and action.

EXAMPLE 14

Production of a Compound Formulation Containing Phyllodulcin

A liver function protecting or improving agent was produced by mixing the following composition.

| | |
|---|---|
| Phyllodulcin produced in Example 1 | 4.9 g |
| Pine-dex #3 | 4.9 g |
| Iron (III) pyrophosphate (iron source; Kokusan Chemical Co., Ltd.) | 0.01 g |
| Phoscal EFC (calcium source; Nikko Fine Products) | 0.1 g |
| Vitamin Mix (Merck & Co., Inc.) | 0.1 g |

EXAMPLE 15

Production of a Compound Formulation Containing Hydrangenol

A liver function protecting or improving agent was produced by mixing the following composition.

| | |
|---|---|
| Hydrangenol produced in Example 2 | 4.9 g |
| Pine-dex #3 | 4.9 g |

| -continued | |
|---|---|
| Iron (III) pyrophosphate (iron source; Kokusan Chemical Co., Ltd.) | 0.01 g |
| Phoscal EFC (calcium source; Nikko Fine Products) | 0.1 g |
| Vitamin Mix (Merck & Co., Inc.) | 0.1 g |

EXAMPLE 16

Production of a Compound Formulation Containing Thunberginol A

A liver function protecting or improving agent was produced by mixing the following composition.

| | |
|---|---|
| Thunberginol A produced in Example 3 | 0.49 g |
| Pine-dex #3 | 0.49 g |
| Iron (III) pyrophosphate (iron source; Kokusan Chemical Co., Ltd.) | 0.001 g |
| Phoscal EFC (calcium source; Nikko Fine Products) | 0.01 g |
| Vitamin Mix (Merck & Co., Inc.) | 0.01 g |

EXAMPLE 17

The liver function protecting or improving agent produced in Example 16 in an amount of 1 g was dispersed into 10 ml of water to produce a drink for protecting or improving a liver function.

EXAMPLE 18

Production of a Cake Including Phyllodulcin

Cookies (30 pieces) were prepared from the following ingredients.

| | |
|---|---|
| Soft flour | 100 g |
| Starch | 74 g |

| -continued | |
|---|---|
| Water | 14 g |
| Phyllodulcin produced in Example 1 | 3 g |
| Baking powder | 2 Tsp. |
| Salt | 2 Tsp. |
| Egg | 1 |
| Butter | 80 g |
| Milk | 2 Tbsp. |

INDUSTRIAL APPLICABILITY

According to the present invention, a liver function protecting or improving agent, a food and drink or a feed for protecting or improving liver functions, and an additive for foods and drinks or an additive for feeds having a liver function protecting or improving activity can be provided.

The invention claimed is:

1. A method for suppressing hepatopathy induced by viruses or ethanol, which comprises administering a therapeutically effective amount of at least one member selected from the group consisting of phyllodulcin, hydrangenol and thunberginol A, a glycoside thereof, and a pharmaceutically acceptable salt thereof, to an animal including human.

2. The method according to claim 1, wherein said at least one member is phyllodulcin.

3. The method according to claim 1, wherein said at least one member is hydrangenol.

4. The method according to claim 1, wherein said method is for suppressing hepatopathy induced by viruses.

5. The method according to claim 4, wherein said method is for suppressing hepatopathy induced by ethanol.

6. The method according to claim 2, wherein said method is for suppressing hepatopathy induced by viruses.

7. The method according to claim 2, wherein said method is for suppressing hepatopathy induced by ethanol.

8. The method according to claim 3, wherein said method is for suppressing hepatopathy induced by viruses.

9. The method according to claim 3, wherein said method is for suppressing hepatopathy induced by ethanol.

* * * * *